(12) United States Patent
Hubschwerlen et al.

(10) Patent No.: US 10,087,171 B2
(45) Date of Patent: Oct. 2, 2018

(54) CRYSTALLINE FORMS OF CADAZOLID

(71) Applicant: ACTELION PHARMACEUTICALS LTD, Allschwil (CH)

(72) Inventors: Christian Hubschwerlen, Durmenach (FR); Philippe Panchaud, Allschwil (CH); Timo Rager, Herznach (CH); Jean-Luc Specklin, Kembs (FR)

( * ) Notice: Subject to any disclaimer, the term of this patent is extended or adjusted under 35 U.S.C. 154(b) by 0 days.

(21) Appl. No.: 15/845,860

(22) Filed: Dec. 18, 2017

(65) Prior Publication Data

US 2018/0179196 A1 Jun. 28, 2018

(30) Foreign Application Priority Data

Dec. 19, 2016 (EP) ..................................... 16205064

(51) Int. Cl.
C07D 413/14 (2006.01)
A61P 31/04 (2006.01)

(52) U.S. Cl.
CPC ............ C07D 413/14 (2013.01); *A61P 31/04* (2018.01); *C07B 2200/13* (2013.01)

(58) Field of Classification Search
CPC .... C07D 413/14; A61P 31/04; C07B 2200/13
USPC ......................................................... 514/312
See application file for complete search history.

(56) References Cited

U.S. PATENT DOCUMENTS

| 4,461,773 | A | 7/1984 | Gregory et al. |
| 4,806,541 | A | 2/1989 | Jolidon et al. |
| 6,689,769 | B2 | 2/2004 | Gordeev et al. |
| 7,820,823 | B2 | 10/2010 | Hubschwerlen et al. |
| 8,039,466 | B2 | 10/2011 | Hubschwerlen et al. |
| 8,124,623 | B2 * | 2/2012 | Hubschwerlen ..... C07D 471/04 514/312 |
| 2004/0132674 | A1 | 7/2004 | Reske-Kunz et al. |
| 2010/0222302 | A1 | 9/2010 | Hubschwerlen et al. |

FOREIGN PATENT DOCUMENTS

| AU | 2004 270379 | 3/2005 |
| EP | 0 241 206 | 10/1987 |
| EP | 0 550 025 | 7/1993 |
| JP | 04128288 | 4/1992 |
| KR | 2000-0067306 | 11/2000 |
| SU | 1156597 | 5/1985 |
| WO | WO 1988/07998 | 10/1988 |
| WO | WO 2001/042242 | 6/2001 |
| WO | WO 2002/059116 | 8/2002 |
| WO | WO 2002/064574 | 8/2002 |
| WO | WO 2003/002560 | 1/2003 |
| WO | WO 2003//031443 | 4/2003 |
| WO | WO 2003/032962 | 4/2003 |
| WO | WO 2003/064415 | 8/2003 |
| WO | WO 2004/096221 | 11/2004 |
| WO | WO 2005/023801 | 3/2005 |
| WO | WO 2005/058886 | 6/2005 |
| WO | WO 2005/058888 | 6/2005 |
| WO | WO 2007/017828 | 2/2007 |
| WO | WO 2007/023507 | 3/2007 |
| WO | WO 2008/056335 | 5/2008 |
| WO | WO 2008/062379 | 5/2008 |
| WO | WO 2009/136379 | 11/2009 |
| WO | WO 2016/079757 | 5/2016 |

OTHER PUBLICATIONS

Borredon et al., "Epoxyoation En Milieu Heterogene Solide-Liquide: Effet Des Interactions a L'interface Sur La Stabilite De L'ylure De Dimethylsulfonium—Consequences Sur La Stereochimiede La Reaction D'epoxydation", Tetrahedron Letters, vol. 2(17), p. 1877-1880, (1987).

Brickner Steven, "Oxazolidinoe Antibacterial Agents", Current Pharmaceutical Design, vol. 2, p. 175-194, (1996).

Corey et al., "Dimethyloxosulfonium Methylide (($CH_3)_2SOCH_2$) and Dimethylsulfonium Methylide ( ($CH_3)_2SCH_2$) Formation and Application to Organic Synthesis", Journal of the American Chemical Society, vol. 87(6), p. 1353-1364, (1965).

Eustice et al., "An Automated Pulse Labelling Method for Structure-Activity Relationship Studies with Antibacterial Oxazolidinones", Drugs Exptl. Clin. Res., vol. 4, p. 149-155, (1990).

Gibson et al., "Preformulation and Formulation—A Practical Guide from Candidate Drug Selection to Commercial Dosage Formulation", HIS Health Group, (2001).

Gould et al., "Salt selection for basic drugs", International Journal of Pharmaceutics, vol. 33, p. 201-217, (1986).

Gregory et al., "Antibacterials. Synthesis and Structure-Activity Studies of 3-Aryl-2-oxooxazolidines. 1. The "B" Group", Journal of Medicinal Chemistry, vol. 32(8), p. 1673-1681, (1989).

Hamilton-Miller et al., "Dual-action antibiotic hybrids", J. Antimicrob Chemother., vol. 33, p. 197-200, (1994).

Hubschwerlen et al., "Design, Synthesis and Biological Evaluation of Oxazolidinone—Quinolone Hybrids", Bioorganic & Medicinal Chemistry, vol. 11, p. 2313-2319, (2003).

Hubschwerlen et al., "Structure-Activity Relationship in the Oxazolidinone-Quinolone Hybrid Series: Influence of the Central Spacer on the Antibacterial Activity and the Mode of Action", Bioorganic & Medicinal Chemistry Letters, vol. 13, p. 4229-4233, (2003).

Jacobsen et al., "Asymmetric Dihydroxylation via Ligand-Accelerated Catalysis", American Chemical Society, vol. 110(6), p. 1968-1970, (1988).

Kocienski Philip, "Protecting Groups", University of Southampton-Department of Chemistry, (1994).

Mitsunobu Oyo, "The Use of Diethyl Azodicarboxylate and Triphenylphosphine in Synthesis and Transformation of Natural Products", Synthesis, p. 1-28, (1981).

"NCT01222702", Efficacy, Safety and Tolerability of Cadazolid in Subjects With Clostridium Difficile (CDAD), U.S. National Library of Medicine (accessed on Mar. 16, 2018: https://clinicaltrials.gov).

"NCT01987895", Efficacy and Safety of Cadazolid Versus Vancomycin in Subjects With Clostridium Difficile—Associated Diarrhea (CDAD), U.S. National Library of Medicine (accessed on Mar. 16, 2018: https://clinicaltrials.gov).

(Continued)

*Primary Examiner* — Yong L Chu
(74) *Attorney, Agent, or Firm* — Hoxie & Associates LLC

(57) ABSTRACT

The present invention relates to crystalline forms of cadazolid.

16 Claims, 2 Drawing Sheets

(56) References Cited

OTHER PUBLICATIONS

Ranaldi et al., "Transport of the Antibacterial Agent Oxazolidin-2-One and Derivatives across Intestinal (Caco-2) and Renal (MDCK) Epithelial Cell Lines", Antimicrobial Agents and Chemotherapy, vol. 40(3), p. 652-658, (1996).
Remington, "The Science and Practice of Pharmacy", 21st Ed., Part 5, Pharmaceutical Manufacturing, (2005).
Remington, The Science and Practice of Pharmacy, 20th Edition (2001).
Rudra et al., "Synthesis and antibacterial activity of novel oxazolidinones with methylene oxygen- and methylene sulfur-linked substituents at C5-position", Bioorganic & Medicinal Chemistry Letters, vol. 17, p. 4778-4783, (2007).
Sakurai et al., "Synthesis and Structure-Activity Relationships of 7-(2-Aminoalkyl) Morpholinoquinolones as Anti-Helicobacter Pylori Agents", Bioorganic & Medicinal Chemistry Letters, vol. 8, p. 2185-2190, (1998).
Vera-Cabrera et al., "In Vitro Activities of the Novel Oxazolidinones DA-7867 and DA-7157 against Rapidly and Slowly Growing Mycobacteria", Antimicrobial Agents and Chemotherapy, vol. 50(12), p. 4027-4029, (2006).
Vera-Cabrera et al., "In Vitro Activities of DA-7157 and DA-7218 against *Mycobacterium tuberculosis* and *Nocardia brasiliensis*", Antimicrobial Agents and Chemotherapy, vol. 50(9), p. 3170-3172, (2006).
Yoon et al., "In Vitro and In Vivo Activities of DA-7867, a New Oxazolidinone, against Aerobic Gram-Positive Bacteria", Antimicrobial Agents and Chemotherapy, vol. 49(6), p. 2498-2500, (2005).
Yu, Lian, "Inferring Thermodynamic Stability Relationship of Polymorphs from Melting Data", Journal of Pharmaceuticals Sciences, vol. 84(8), p. 966-974, (1995).

* cited by examiner

CRYSTALLINE FORMS OF CADAZOLID

CROSS REFERENCE TO RELATED APPLICATIONS

This application claims priority and the benefit of European Patent Application No. EP 16205064.5, filed on Dec. 19, 2016, the contents of each of which are incorporated herein by reference.

The present invention relates to crystalline forms of 1-cyclopropyl-6-fluoro-7-{4-[2-fluoro-4-((R)-5-hydroxymethyl-2-oxo-oxazolidin-3-yl)-phenoxymethyl]-4-hydroxypiperidin-1-yl}-4-oxo-1,4-dihydro-quinoline-3-carboxylic acid (CAS RN 1025097-10-2; hereinafter referred to as "cadazolid"), which belongs to the class of antimicrobial drugs. The current invention further relates to pharmaceutical compositions comprising crystalline forms of cadazolid and their use as a medicament, notably as antimicrobial agents effective against a variety of human and veterinary pathogens such as *Clostridium difficile, Clostridium perfringens* and *Staphylococcus aureus*.

Cadazolid and its antimicrobial activity have been previously described in WO2008056335 and WO2009136379. Clinical aspects of its antibiotic activity in humans have been investigated (https://clinicaltrials.gov; e.g. NCT01222702 and NCT01987895).

The aim of the present invention was the provision of crystalline forms of cadazolid which have advantageous properties.

Figure 1:
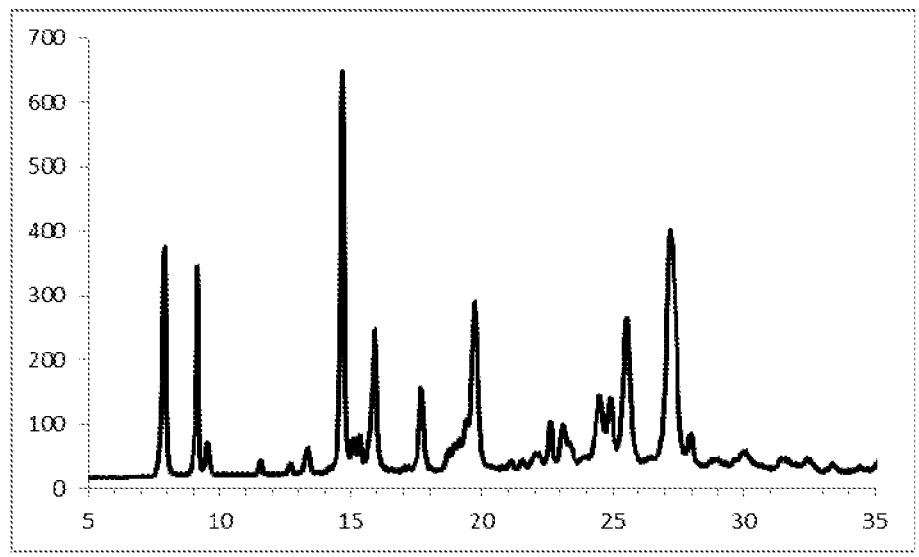
FIG. 1 shows the X-ray powder diffraction diagram of cadazolid in crystalline form A, wherein the X-ray powder diffraction diagram is displayed against Cu Kα radiation. In the diagram the angle of refraction 2θ is plotted on the horizontal axis and the intensity (cps) on the vertical axis. The X-ray diffraction diagram shows peaks having a relative intensity, as compared to the most intense peak in the diagram, of the following percentages (relative peak intensities given in parenthesis) at the indicated angles of refraction 2theta (selected peaks from the range 3-30° 2theta with relative intensity larger than 10% are reported): 7.9° (55%), 9.1° (52%), 14.7° (100%), 15.9° (34%), 17.7° (20%), 19.7° (41%), 24.5° (15%), 24.9° (15%), 25.5° (35%), and 27.2° (56%).
Figure 2:
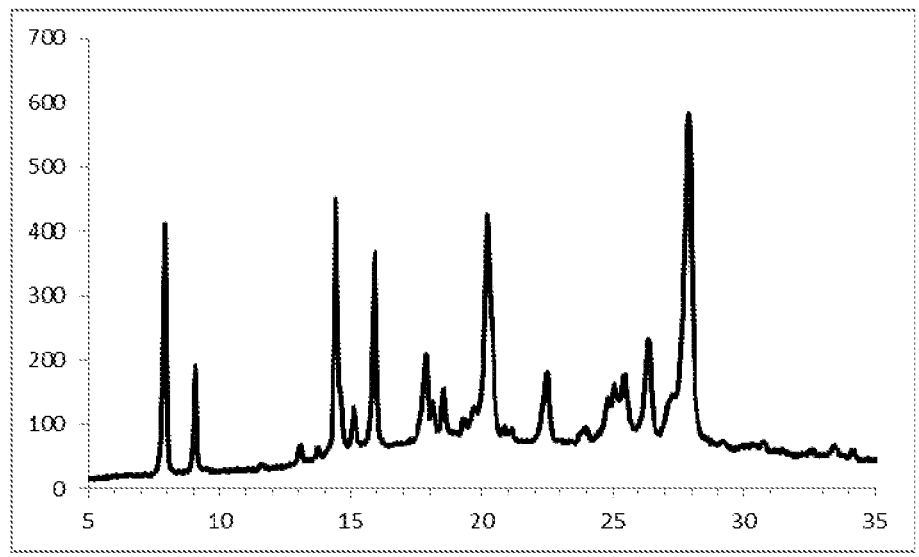
FIG. 2 shows the X-ray powder diffraction diagram of cadazolid in crystalline form B, wherein the X-ray powder diffraction diagram is displayed against Cu Kα radiation. In the diagram the angle of refraction 2θ is plotted on the horizontal axis and the intensity (cps) on the vertical axis. The X-ray diffraction diagram shows peaks having a relative intensity, as compared to the most intense peak in the diagram, of the following percentages (relative peak intensities given in parenthesis) at the indicated angles of refraction 2theta (selected peaks from the range 3-30° 2theta with relative intensity larger than 10% are reported): 7.9° (71%), 9.1° (32%), 14.4° (78%), 15.1° (12%), 15.9° (59%), 17.9° (24%), 18.5° (13%), 20.2° (66%), 22.5° (19%), 25.1° (14%), 25.4° (17%), 26.4° (28%), 27.3° (11%), and 27.9° (100%).
Figure 3:
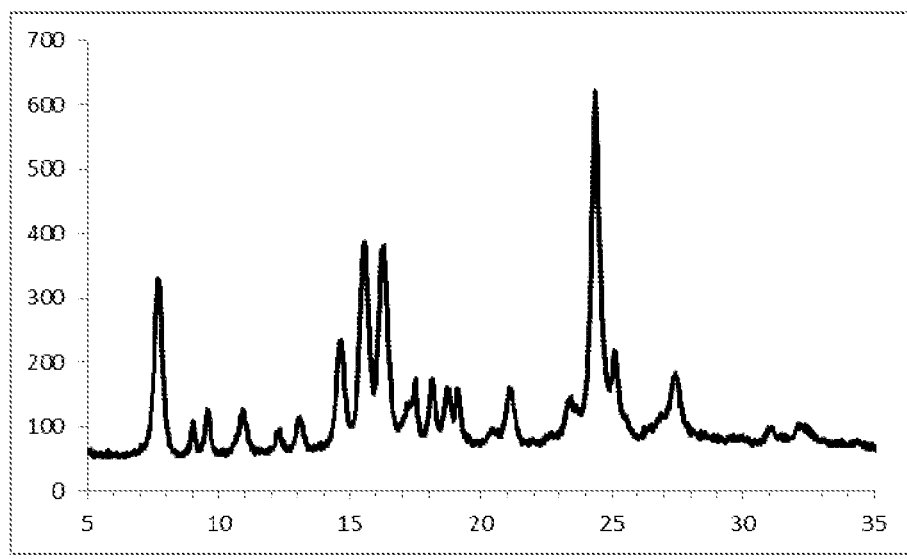
FIG. 3 shows the X-ray powder diffraction diagram of cadazolid in crystalline form C, wherein the X-ray powder diffraction diagram is displayed against Cu Kα radiation. In the diagram the angle of refraction 2θ is plotted on the horizontal axis and the intensity (cps) on the vertical axis. The X-ray diffraction diagram shows peaks having a relative intensity, as compared to the most intense peak in the diagram, of the following percentages (relative peak intensities given in parenthesis) at the indicated angles of refraction 2theta (selected peaks from the range 3-30° 2theta with relative intensity larger than 10% are reported): 7.7° (50%), 10.9° (11%), 14.6° (26%), 15.5° (55%), 16.3° (51%), 17.5° (13%), 18.1° (14%), 18.7° (12%), 19.1° (13%), 21.1° (13%), 24.4° (100%), 25.1° (22%), and 27.4° (16%).

For the avoidance of any doubt, the above-listed peaks describe the experimental results of the X-ray powder diffraction shown in FIGS. 1 to 3. It is understood that, in contrast to the above peak list, only a selection of characteristic peaks is required to fully and unambiguously characterize cadazolid in the respective crystalline form of the present invention.

DESCRIPTION OF THE INVENTION

1) A first embodiment of the invention relates to cadazolid in crystalline form A, characterized by an X-ray powder diffraction pattern having peaks at the following angles of refraction 2θ: 7.9°, 14.7°, and 27.2°, wherein the X-ray powder diffraction pattern is measured using a Cu Kα (1.5418 Å) source.

2) Another embodiment of the invention relates to cadazolid in crystalline form A, characterized by an X-ray powder diffraction pattern having peaks at the following angles of refraction 2θ: 7.9°, 9.1°, 14.7°, 19.7° and 27.2°, wherein the X-ray powder diffraction pattern is measured using a Cu Kα (1.5418 Å) source.

3) Another embodiment of the invention relates to cadazolid in crystalline form A, characterized by an X-ray powder diffraction pattern having peaks at the following angles of refraction 2θ: 7.9°, 9.1°, 14.7°, 15.9°, 17.7°, 19.7°, 24.5°, 24.9°, 25.5° and 27.2°, wherein the X-ray powder diffraction pattern is measured using a Cu Kα (1.5418 Å) source.

4) Another embodiment of the invention relates to cadazolid in crystalline form A, which essentially shows the X-ray powder diffraction pattern as depicted in FIG. 1.

5) Another embodiment of the invention relates to cadazolid in crystalline form A, according to any one of embodiments 1) to 4), characterized by a melting point of about 239° C. as determined by differential scanning calorimetry using the method as described herein.

6) Another embodiment of the invention relates to cadazolid in crystalline form A, obtainable by:
   a) dissolving 92.7 g of cadazolid in 184 mL hot DMSO;
   b) diluting the resulting solution with 368 mL boiling water;
   c) allowing to cool to room temperature and further cooling to 5° C.; and
   d) filtering, washing with water and drying under vacuum.

7) Another embodiment of the invention relates to cadazolid in crystalline form A according to embodiment 6), characterized by an X-ray powder diffraction pattern having peaks at the following angles of refraction 2θ: 7.9°, 14.7° and 27.2°, wherein the X-ray powder diffraction pattern is measured using a Cu Kα (1.5418 Å) source.

8) Another embodiment of the invention relates to cadazolid in crystalline form A according to embodiment 6), characterized by an X-ray powder diffraction pattern having peaks at the following angles of refraction 2θ: 7.9°, 9.1°, 14.7°, 19.7° and 27.2°, wherein the X-ray powder diffraction pattern is measured using a Cu Kα (1.5418 Å) source.

9) Another embodiment of the invention relates to cadazolid in crystalline form A according to embodiment 6), characterized by an X-ray powder diffraction pattern having peaks at the following angles of refraction 2θ: 7.9°, 9.1°, 14.7°, 15.9°, 17.7°, 19.7°, 24.5°, 24.9°, 25.5° and 27.2°, wherein the X-ray powder diffraction pattern is measured using a Cu Kα (1.5418 Å) source.

10) Another embodiment of the invention relates to cadazolid in crystalline form A according to any one of embodiments 6) to 9), characterized by a melting point of about 239° C. as determined by differential scanning calorimetry using the method as described herein.

11) Another embodiment of the invention relates to a composition comprising the cadazolid in crystalline form A according to any one of embodiments 1) to 10), further comprising at least one pharmaceutically acceptable excipient.

12) Another embodiment of the invention relates to cadazolid in crystalline form A according to any one of embodiments 1) to 10), or a composition according to embodiment 11), for use as a medicament.

13) Another embodiment of the invention relates to cadazolid in crystalline form A according to any one of embodiment 1) to 10), or a composition according to embodiment 11), for use in the treatment or prevention, preferably in the treatment, of a bacterial disease.

14) Another embodiment of the invention relates to cadazolid in crystalline form A according to any one of embodiments 1) to 10), or a composition according to embodiment 11), for use in the treatment or prevention, preferably in the treatment, of a bacterial disease mediated by *Clostridium difficile, Clostridium perfringens* or *Staphylococcus aureus*.

15) Another embodiment of the invention relates to cadazolid in crystalline form A according to any one of embodiments 1) to 10), or a composition according to embodiment 11), for use in the treatment or prevention, preferably in the treatment, of a bacterial disease mediated by *Clostridium difficile*.

16) Another embodiment of the invention relates to cadazolid in crystalline form B, characterized by an X-ray powder diffraction pattern having peaks at the following angles of refraction 2θ: 7.9°, 14.4° and 27.9°, wherein the X-ray powder diffraction pattern is measured using a Cu Kα (1.5418 Å) source.

17) Another embodiment of the invention relates to cadazolid in crystalline form B, characterized by an X-ray powder diffraction pattern having peaks at the following angles of refraction 2θ: 7.9°, 14.4°, 15.9°, 20.2°, and 27.9°, wherein the X-ray powder diffraction pattern is measured using a Cu Kα (1.5418 Å) source.

18) Another embodiment of the invention relates to cadazolid in crystalline form B, characterized by an X-ray powder diffraction pattern having peaks at the following angles of refraction 2θ: 7.9°, 9.1°, 14.4°, 15.9°, 17.9°, 18.5°, 20.2°, 22.5°, 26.4° and 27.9°, wherein the X-ray powder diffraction pattern is measured using a Cu Kα (1.5418 Å) source.

19) Another embodiment of the invention relates to cadazolid in crystalline form B, which essentially shows the X-ray powder diffraction pattern as depicted in FIG. 2.

20) Another embodiment of the invention relates to cadazolid in crystalline form B, obtainable by:
a) stirring a suspension of 198 mg of cadazolid form A in 2 mL of water at room temperature for 3 days; and
b) filtering off the solid.

21) Another embodiment of the invention relates to cadazolid in crystalline form B, obtainable by:
a) agitating a suspension of 27 mg cadazolid form A and 25 mg cadazolid form C in 1 mL H$_2$O at 25° C. for 5 days; and
b) filtering off the solid.

22) Another embodiment of the invention relates to cadazolid in crystalline form B according to embodiment 20) or 21), characterized by an X-ray powder diffraction pattern having peaks at the following angles of refraction 2θ: 7.9°, 14.4° and 27.9°, wherein the X-ray powder diffraction pattern is measured using a Cu Kα (1.5418 Å) source.

23) Another embodiment of the invention relates to cadazolid in crystalline form B according to embodiment 20) or 21), characterized by an X-ray powder diffraction pattern having peaks at the following angles of refraction 2θ: 7.9°, 14.4°, 15.9°, 20.2°, and 27.9°, wherein the X-ray powder diffraction pattern is measured using a Cu Kα (1.5418 Å) source.

24) Another embodiment of the invention relates to cadazolid in crystalline form B according to embodiment 20) or 21), characterized by an X-ray powder diffraction pattern having peaks at the following angles of refraction 2θ: 7.9°, 9.1°, 14.4°, 15.9°, 17.9°, 18.5°, 20.2°, 22.5°, 26.4° and 27.9°, wherein the X-ray powder diffraction pattern is measured using a Cu Kα (1.5418 Å) source.

25) Another embodiment of the invention relates to a composition comprising the cadazolid in crystalline form B according to any one of embodiments 16) to 24), further comprising at least one pharmaceutically acceptable excipient.

26) Another embodiment of the invention relates to cadazolid in crystalline form B according to any one of embodiments 16) to 24), or a composition according to embodiment 25), for use as a medicament.

27) Another embodiment of the invention relates to cadazolid in crystalline form B according to any one of embodiments 16) to 24), or a composition according to embodiment 25), for use in the treatment or prevention, preferably in the treatment, of a bacterial disease.

28) Another embodiment of the invention relates to cadazolid in crystalline form B according to any one of embodiments 16) to 24), or a composition according to embodiment 25), for use in the treatment or prevention, preferably in the treatment, of a bacterial disease mediated by *Clostridium difficile, Clostridium perfringens* or *Staphylococcus aureus*.

29) Another embodiment of the invention relates to cadazolid in crystalline form B according to any one of embodiments 16) to 24), or a composition according to embodiment 25), for use in the treatment or prevention, preferably in the treatment, of a bacterial disease mediated by *Clostridium difficile*.

30) Another embodiment of the invention relates to cadazolid in crystalline form C, characterized by an X-ray powder diffraction pattern having peaks at the following angles of refraction 2θ: 7.7°, 15.5° and 24.4°, wherein the X-ray powder diffraction pattern is measured using a Cu Kα (1.5418 Å) source.
31) Another embodiment of the invention relates to cadazolid in crystalline form C, characterized by an X-ray powder diffraction pattern having peaks at the following angles of refraction 2θ: 7.7°, 14.6°, 15.5°, 16.3° and 24.4°, wherein the X-ray powder diffraction pattern is measured using a Cu Kα (1.5418 Å) source.
32) Another embodiment of the invention relates to cadazolid in crystalline form C, characterized by an X-ray powder diffraction pattern having peaks at the following angles of refraction 2θ: 7.7°, 10.9°, 14.6°, 15.5°, 16.3°, 18.1°, 21.1°, 24.4°, 25.1° and 27.4°, wherein the X-ray powder diffraction pattern is measured using a Cu Kα (1.5418 Å) source.
33) Another embodiment of the invention relates to cadazolid in crystalline form C, which essentially shows the X-ray powder diffraction pattern as depicted in FIG. 3.
34) Another embodiment of the invention relates to cadazolid in crystalline form C according to any one of embodiments 30) to 33), characterized by a melting point of about 221° C. as determined by differential scanning calorimetry using the method as described herein.
35) Another embodiment of the invention relates to cadazolid in crystalline form C, obtainable by:
   a) dissolving 80 mg of cadazolid form A in 0.5 mL DMSO;
   b) adding the solution of step (a) to 10 mL isopropanol while stirring; and
   c) filtering off after 2 min, washing with isopropanol and drying for 30 min at room temperature and 3 mbar vacuum.
36) Another embodiment of the invention relates to cadazolid in crystalline form C according to embodiment 35), characterized by an X-ray powder diffraction pattern having peaks at the following angles of refraction 2θ: 7.7°, 15.5° and 24.4°, wherein the X-ray powder diffraction pattern is measured using a Cu Kα (1.5418 Å) source.
37) Another embodiment of the invention relates to cadazolid in crystalline form C according to embodiment 35), characterized by an X-ray powder diffraction pattern having peaks at the following angles of refraction 2θ: 7.7°, 14.6°, 15.5°, 16.3° and 24.4°, wherein the X-ray powder diffraction pattern is measured using a Cu Kα (1.5418 Å) source.
38) Another embodiment of the invention relates to cadazolid in crystalline form C according to embodiment 35), characterized by an X-ray powder diffraction pattern having peaks at the following angles of refraction 2θ: 7.7°, 10.9°, 14.6°, 15.5°, 16.3°, 18.1°, 21.1°, 24.4°, 25.1° and 27.4°, wherein the X-ray powder diffraction pattern is measured using a Cu Kα (1.5418 Å) source.
39) Another embodiment of the invention relates to cadazolid in crystalline form C according to any one of embodiments 35) to 38), characterized by a melting point of about 221° C. as determined by differential scanning calorimetry using the method as described herein.
40) Another embodiment of the invention relates to a composition comprising the cadazolid in crystalline form C according to any one of embodiments 30) to 39), further comprising at least one pharmaceutically acceptable excipient.
41) Another embodiment of the invention relates to cadazolid in crystalline form C according to any one of embodiments 30) to 39), or a composition according to embodiment 40), for use as a medicament.
42) Another embodiment of the invention relates to cadazolid in crystalline form C according to any one of embodiments 30) to 39), or a composition according to embodiment 40), for use in the treatment or prevention, preferably in the treatment, of a bacterial disease.
43) Another embodiment of the invention relates to cadazolid in crystalline form C according to any one of embodiments 30) to 39), or a composition according to embodiment 40), for use in the treatment or prevention, preferably in the treatment, of a bacterial disease mediated by *Clostridium difficile*, *Clostridium perfringens* or *Staphylococcus aureus*.
44) Another embodiment of the invention relates to cadazolid in crystalline form C according to any one of embodiments 30) to 39), or a composition according to embodiment 40), for use in the treatment or prevention, preferably in the treatment, of a bacterial disease mediated by *Clostridium difficile*.

Based on the dependencies of the different embodiments 1) to 44) as disclosed hereinabove, the following embodiments are thus possible and intended and herewith specifically disclosed in individualized form:

5+1, 5+2, 5+3, 5+4, 7+6, 8+6, 9+6, 10+6, 10+7+6, 10+8+6, 10+9+6, 11+1, 11+2, 11+3, 11+4, 11+5+1, 11+5+2, 11+5+3, 11+5+4, 11+6, 11+7+6, 11+8+6, 11+9+6, 11+10+6, 11+10+7+6, 11+10+8+6, 11+10+9+6, 12+1, 12+2, 12+3, 12+4, 12+5+1, 12+5+2, 12+5+3, 12+5+4, 12+6, 12+7+6, 12+8+6, 12+9+6, 12+10+6, 12+10+7+6, 12+10+8+6, 12+10+9+6, 12+11+1, 12+11+2, 12+11+3, 12+11+4, 12+11+5+1, 12+11+5+2, 12+11+5+3, 12+11+5+4, 12+11+6, 12+11+7+6, 12+11+8+6, 12+11+9+6, 12+11+10+6, 12+11+10+7+6, 12+11+10+8+6, 12+11+10+9+6, 13+1, 13+2, 13+3, 13+4, 13+5+1, 13+5+2, 13+5+3, 13+5+4, 13+6, 13+7+6, 13+8+6, 13+9+6, 13+10+6, 13+10+7+6, 13+10+8+6, 13+10+9+6, 13+11+1, 13+11+2, 13+11+3, 13+11+4, 13+11+5+1, 13+11+5+2, 13+11+5+3, 13+11+5+4, 13+11+6, 13+11+7+6, 13+11+8+6, 13+11+9+6, 13+11+10+6, 13+11+10+7+6, 13+11+10+8+6, 13+11+10+9+6, 14+1, 14+2, 14+3, 14+4, 14+5+1, 14+5+2, 14+5+3, 14+5+4, 14+6, 14+7+6, 14+8+6, 14+9+6, 14+10+6, 14+10+7+6, 14+10+8+6, 14+10+9+6, 14+11+1, 14+11+2, 14+11+3, 14+11+4, 14+11+5+1, 14+11+5+2, 14+11+5+3, 14+11+5+4, 14+11+6, 14+11+7+6, 14+11+8+6, 14+11+9+6, 14+11+10+6, 14+11+10+7+6, 14+11+10+8+6, 14+11+10+9+6, 15+1, 15+2, 15+3, 15+4, 15+5+1, 15+5+2, 15+5+3, 15+5+4, 15+6, 15+7+6, 15+8+6, 15+9+6, 15+10+6, 15+10+7+6, 15+10+8+6, 15+10+9+6, 15+11+1, 15+11+2, 15+11+3, 15+11+4, 15+11+5+1, 15+11+5+2, 15+11+5+3, 15+11+5+4, 15+11+6, 15+11+7+6, 15+11+8+6, 15+11+9+6, 15+11+10+6, 15+11+10+7+6, 15+11+10+8+6, 15+11+10+9+6, 22+20, 22+21, 23+20, 23+21, 24+20, 24+21, 25+16, 25+17, 25+18, 25+19, 25+20, 25+21, 25+22+20, 25+22+21, 25+23+20, 25+23+21, 25+24+20, 25+24+21, 26+16, 26+17, 26+18, 26+19, 26+20, 26+21, 26+22+20, 26+22+21, 26+23+20, 26+23+21, 26+24+20, 26+24+21, 26+25+16, 26+25+17, 26+25+18, 26+25+19, 26+25+20, 26+25+21, 26+25+22+20, 26+25+22+21, 26+25+23+20, 26+25+23+21, 26+25+24+20, 26+25+24+21, 27+16, 27+17, 27+18, 27+19, 27+20, 27+21, 27+22+20, 27+22+21, 27+23+20, 27+23+21, 27+24+20, 27+24+21, 27+25+16, 27+25+17, 27+25+18, 27+25+19, 27+25+20, 27+25+21, 27+25+22+20, 27+25+22+21, 27+25+23+20, 27+25+23+21, 27+25+24+20, 27+25+24+21, 28+16, 28+17, 28+18, 28+19, 28+20, 28+21, 28+22+20, 28+22+21, 28+23+20, 28+23+21, 28+24+20, 28+24+21, 28+25+16, 28+25+17, 28+25+18, 28+25+19,

28+25+20, 28+25+21, 28+25+22+20, 28+25+22+21, 28+25+23+20, 28+25+23+21, 28+25+24+20, 28+25+24+21, 29+16, 29+17, 29+18, 29+19, 29+20, 29+21, 29+22+20, 29+22+21, 29+23+20, 29+23+21, 29+24+20, 29+24+21, 29+25+16, 29+25+17, 29+25+18, 29+25+19, 29+25+20, 29+25+21, 29+25+22+20, 29+25+22+21, 29+25+23+20, 29+25+23+21, 29+25+24+20, 29+25+24+21, 34+30, 34+31, 34+32, 34+33, 36+35, 37+35, 38+35, 39+35, 39+36+35, 39+37+35, 39+38+35, 40+30, 40+31, 40+32, 40+33, 40+34+30, 40+34+31, 40+34+32, 40+34+33, 40+35, 40+36+35, 40+37+35, 40+38+35, 40+39+35, 40+39+36+35, 40+39+37+35, 40+39+38+35, 41+30, 41+31, 41+32, 41+33, 41+34+30, 41+34+31, 41+34+32, 41+34+33, 41+35, 41+36+35, 41+37+35, 41+38+35, 41+39+35, 41+39+36+35, 41+39+37+35, 41+39+38+35, 41+40+30, 41+40+31, 41+40+32, 41+40+33, 41+40+34+30, 41+40+34+31, 41+40+34+32, 41+40+34+33, 41+40+35, 41+40+36+35, 41+40+37+35, 41+40+38+35, 41+40+39+35, 41+40+39+36+35, 41+40+39+37+35, 41+40+39+38+35, 42+30, 42+31, 42+32, 42+33, 42+34+30, 42+34+31, 42+34+32, 42+34+33, 42+35, 42+36+35, 42+37+35, 42+38+35, 42+39+35, 42+39+36+35, 42+39+37+35, 42+39+38+35, 42+40+30, 42+40+31, 42+40+32, 42+40+33, 42+40+34+30, 42+40+34+31, 42+40+34+32, 42+40+34+33, 42+40+35, 42+40+36+35, 42+40+37+35, 42+40+38+35, 42+40+39+35, 42+40+39+36+35, 42+40+39+37+35, 42+40+39+38+35, 43+30, 43+31, 43+32, 43+33, 43+34+30, 43+34+31, 43+34+32, 43+34+33, 43+35, 43+36+35, 43+37+35, 43+38+35, 43+39+35, 43+39+36+35, 43+39+37+35, 43+39+38+35, 43+40+30, 43+40+31, 43+40+32, 43+40+33, 43+40+34+30, 43+40+34+31, 43+40+34+32, 43+40+34+33, 43+40+35, 43+40+36+35, 43+40+37+35, 43+40+38+35, 43+40+39+35, 43+40+39+36+35, 43+40+39+37+35, 43+40+39+38+35, 44+30, 44+31, 44+32, 44+33, 44+34+30, 44+34+31, 44+34+32, 44+34+33, 44+35, 44+36+35, 44+37+35, 44+38+35, 44+39+35, 44+39+36+35, 44+39+37+35, 44+39+38+35, 44+40+30, 44+40+31, 44+40+32, 44+40+33, 44+40+34+30, 44+40+34+31, 44+40+34+32, 44+40+34+33, 44+40+35, 44+40+36+35, 44+40+37+35, 44+40+38+35, 44+40+39+35, 44+40+39+36+35, 44+40+39+37+35, and 44+40+39+38+35.

In the list above the numbers refer to the embodiments according to their numbering provided hereinabove whereas "+" indicates the dependency from another embodiment. The different individualized embodiments are separated by commas. In other words, "11+5+1" for example refers to embodiment 11) depending on embodiment 5), depending on embodiment 1), i.e. embodiment "11+5+1" corresponds to embodiment 1) further characterized by the features of the embodiments 5) and 11).

Definitions provided herein are intended to apply uniformly to the subject matter as defined in any one of embodiments 1) to 44), and, mutatis mutandis, throughout the description and the claims unless an otherwise expressly set out definition provides a broader or narrower definition. It is well understood that a definition or a preferred definition of a term or expression defines and may replace the respective term or expression independently of (and in combination with) any definition or preferred definition of any or all other terms or expressions as defined herein.

The crystalline forms of the present invention, i.e. crystalline forms A, B and C of cadazolid, may especially be present in essentially pure form. The expression "in essentially pure form" is understood to mean especially that at least 90, preferably at least 95, and most preferably at least 99 percent by weight of cadazolid is present in a single crystalline form of the present invention.

The term "preventing", "prevent" or "prevention" used with reference to a disease means either that said disease does not occur in the patient or animal, or that, although the animal or patient is affected by the disease, part or all the symptoms of the disease are either reduced or absent.

The term "treating", "treat" or "treatment" used with reference to a disease means either that said disease is cured in the patient or animal, or that, although the animal or patient remains affected by the disease, part or all the symptoms of the disease are either reduced or eliminated.

When defining the presence of a peak in e.g. an X-ray powder diffraction diagram, a common approach is to do this in terms of the S/N ratio (S=signal, N=noise). According to this definition, when stating that an X-ray powder diffraction diagram/pattern has a peak at a certain angle of refraction 2θ, it is understood that the peak in the X-ray powder diffraction diagram/pattern is defined by having an S/N ratio (S=signal, N=noise) of greater than x (x being a numerical value greater than 1), usually greater than 2, especially greater than 3.

In the context with stating that the crystalline form essentially shows an X-ray powder diffraction (XRPD) pattern as depicted in FIG. 1 to FIG. 3, respectively, the term "essentially" means that at least the major peaks of the diagram depicted in said figures, i.e. those having a relative intensity of more than 20%, especially more than 10%, as compared to the most intense peak in the diagram, have to be present. However, the person skilled in the art of X-ray powder diffraction will recognize that relative intensities in X-ray powder diffraction diagrams may be subject to strong intensity variations due to preferred orientation effects.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 5° C. to Y plus 5° C., and preferably to an interval extending from Y minus 3° C. to Y plus 3° C. Room temperature means a temperature of about 23° C.

When specifying an angle of diffraction 2theta (2θ) for a peak in the present application, it should be understood that the value given is to be understood as an interval from said value minus 0.2° to said value plus 0.2°, and preferably from said value minus 0.1° to said value plus 0.1°.

Each one of crystalline forms A, B and C of cadazolid, either as a single component (preferred) or together with other crystalline forms and/or the amorphous form of cadazolid, can be used as a medicament, e.g. in the form of pharmaceutical compositions for enteral administration, especially oral administration, and is suitable for the prevention or treatment of bacterial diseases, especially of bacterial diseases caused by *Clostridium difficile*, *Clostridium perfringens* or *Staphylococcus aureus*, very especially by *Clostridium difficile*.

The production of the pharmaceutical compositions can be effected in a manner which will be familiar to any person skilled in the art (see for example Remington, The Science and Practice of Pharmacy, 21st Edition (2005), Part 5, "Pharmaceutical Manufacturing" [published by Lippincott Williams & Wilkins]) by bringing each one of crystalline forms A, B and C of cadazolid, either as a single component or together with other crystalline forms and/or the amorphous form of cadazolid, optionally in combination with other therapeutically valuable substances, into a galenical administration form together with suitable, non-toxic, inert, pharmaceutically acceptable solid or liquid carrier materials and, if desired, usual pharmaceutical adjuvants.

Each one of crystalline forms A, B and C of cadazolid is active against bacteria. They may therefore be particularly suitable in human, as well as in animals, for the prophylaxis and chemotherapy of local and systemic infections caused by these pathogens as well as disorders related to bacterial infections comprising pneumonia, otitis media, sinusitis, bronchitis, tonsillitis, and mastoiditis related to infection by *Streptococcus pneumoniae, Haemophilus influenzae, Moraxella catarrhalis, Staphylococcus aureus, Enterococcus faecalis, E. faecium, E. casseliflavus, S. epidermidis, S. haemolyticus,* or *Peptostreptococcus* spp.; pharyngitis, rheumatic fever, and glomerulonephritis related to infection by *Streptococcus pyogenes*, Groups C and G streptococci, *Corynebacterium diphtheriae,* or *Actinobacillus haemolyticum*; respiratory tract infections related to infection by *Mycoplasma pneumoniae, Legionella pneumophila, Streptococcus pneumoniae, Haemophilus influenzae,* or *Chlamydia pneumoniae*; blood and tissue infections, including endocarditis and osteomyelitis, caused by *S. aureus, S. haemolyticus, E. faecalis, E. faecium, E. durans,* including strains resistant to known antibacterial actives such as, but not limited to, beta-lactams, vancomycin, aminoglycosides, quinolones, chloramphenicol, tetracyclines and macrolides; uncomplicated skin and soft tissue infections and abscesses, and puerperal fever related to infection by *Staphylococcus aureus*, coagulase-negative staphylococci (i.e., *S. epidermidis, S. haemolyticus*, etc.), *Streptococcus pyogenes, Streptococcus agalactiae*, Streptococcal groups C-F (minute colony streptococci), viridans streptococci, *Corynebacterium minutissimum, Clostridium* spp., or *Bartonella henselae*; uncomplicated acute urinary tract infections related to infection by *Staphylococcus aureus*, coagulase-negative staphylococcal species, or *Enterococcus* spp.; urethritis and cervicitis; sexually transmitted diseases related to infection by *Chlamydia trachomatis, Haemophilus ducreyi, Treponema pallidum, Ureaplasma urealyticum,* or *Neiserria gonorrhoeae*; toxin diseases related to infection by *S. aureus* (food poisoning and toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae,* or *Listeria* spp.; disseminated *Mycobacterium avium* complex (MAC) disease related to infection by *Mycobacterium avium,* or *Mycobacterium intracellulare*; infections caused by *Mycobacterium tuberculosis, M. leprae, M. paratuberculosis, M. kansasii,* or *M. chelonei*; gastroenteritis related to infection by *Campylobacter jejuni*; intestinal protozoa related to infection by *Cryptosporidium* spp.; odontogenic infection related to infection by viridans streptococci; persistent cough related to infection by *Bordetella pertussis*; gas gangrene related to infection by *Clostridium perfringens* or *Bacteroides* spp.; and atherosclerosis or cardiovascular disease related to infection by *Helicobacter pylori* or *Chlamydia pneumoniae*.

Each one of crystalline forms A, B and C of cadazolid is further useful for the prevention or treatment, especially treatment, of infections that are mediated by bacteria such as *E. coli, Klebsiella pneumoniae* and other Enterobacteriaceae, *Acinetobacter* spp., *Stenotrophomonas maltophilia, Neisseria meningitidis, Bacillus cereus, Bacillus anthracis, Corynebacterium* spp., *Propionibacterium acnes* and bacteroide spp.

In addition, each one of crystalline forms A, B and C of cadazolid is useful for the prevention or treatment, especially treatment, of infections that are mediated by *Clostridium difficile, Clostridium perfringens* or *Staphylococcus aureus*.

Each one of crystalline forms A, B and C of cadazolid is further especially useful for the prevention or treatment, especially treatment, of infections that are mediated by *Clostridium difficile*.

Each one of crystalline forms A, B and C of cadazolid is further useful to treat protozoal infections caused by *Plasmodium malaria, Plasmodium falciparum, Toxoplasma gondii, Pneumocystis carinii, Trypanosoma brucei* and *Leishmania* spp.

The preceding lists of pathogens are to be interpreted merely as examples and in no way as limiting. As well as in humans, bacterial infections can also be treated in other species like pigs, ruminants, horses, dogs, cats and poultry.

The present invention also relates to a method for the prevention or treatment, especially treatment, of a disease mentioned herein comprising administering to a subject (especially a human subject) in need thereof a pharmaceutically effective amount of a crystalline form A, B or C of cadazolid.

Each one of crystalline forms A, B and C of cadazolid is further useful for the preparation of a medicament for the prevention or treatment, especially treatment, of a disease mentioned herein.

Experimental Part

Patent applications WO2008056335 and WO2009136379 describe the synthesis of cadazolid. The following Examples illustrate the invention in more detail. Temperatures are given in degrees Celsius. If not stated otherwise percentages are given by weight.

ABBREVIATIONS AS USED HEREIN

ΔS melting entropy
ΔH melting enthalpy
ΔG Gibbs free energy
DMSO dimethylsulfoxid
DSC differential scanning calorimetry
Fig. figure
h hour(s)
$^1$H-NMR proton nuclear magnetic resonance
MeOH methanol
2-PrOH 2-propanol
min minute(s)
m.p. melting point
r.h. relative humidity
r.t. room temperature
XRPD X-ray powder diffraction
cps counts per second Methods Used:
$^1$H-NMR:
400 MHz, Bruker; chemical shifts are given in ppm relative to the solvent used.

X-Ray Powder Diffraction Analysis (XRPD):

X-ray powder diffraction patterns are collected on a Bruker D8 X-ray diffractometer equipped with a Lynxeye detector operated with Cu Kα radiation in reflection mode. Typically, the X-ray tube is run at of 40 kV/40 mA. A step size of 0.02° (2θ) and a step time of 37 sec over a scanning range of 2.5-50° in 2θ are applied. Powders are slightly pressed into a silicon single crystal sample holder with depth of 0.1 mm and samples are rotated in their own plane during the measurement. Diffraction data are reported using Cu Kα (λ=1.5418 Å). The accuracy of the 2θ values as provided herein is in the range of +/−0.1-0.2° as it is generally the case for conventionally recorded X-ray powder diffraction patterns.

For avoidance of any doubt, whenever one of the embodiments herein refers to "an X-ray powder diffraction pattern having peaks at the following angles of refraction 2θ", said X-ray powder diffraction pattern is obtained by using Cu Kα radiation (λ=1.5418 Å); and it should be understood that the accuracy of the 2θ values as provided herein is in the range of +/−0.1-0.2°. Notably, when specifying an angle of refraction 2theta (2θ) for a peak in the invention embodiments and the claims, the 2θ value given is to be understood as an interval from said value minus 0.2° to said value plus 0.2° (2θ+/−0.2°); and preferably from said value minus 0.1° to said value plus 0.1° (2θ+/−0.1°).

Differential Scanning Calorimetry (DSC):

DSC data are collected on a Perkin Elmer DSC 7. The instrument is calibrated for energy and temperature using certified indium. Samples are sealed in hermetically closed gold crucibles under $N_2$, heating rates of 10° C./min or 100° C./min, scan from −50° C. to variable end temperatures. Peak temperatures are reported for melting points.

Gravimetric Water Vapor Sorption Analysis (GVS):

GVS1: Projekt Messtechnik SPS 11-100n water vapor sorption analyzer. The samples are placed in aluminum crucibles on top of a microbalance. They are equilibrated at 25° C. and 50% r.h. and are then subjected to a pre-defined humidity program at 25° C. in the order 50-0-95-50% r.h. A scanning rate of r.h.=5%/h is used and 'isohumid' equilibration periods are included at the extreme values.

GVS2: Surface Measurement Systems Ltd. DVS-1 water vapor sorption analyzer. The sample is placed in a Pt pan suspended on a micro balance and is exposed to a $N_2$ flow with 95% r.h. at the beginning and then decreasing with a constant rate of 5%/h.

Example 1.1: Preparation of Crystalline Form A of Cadazolid 92.7 g of cadazolid are dissolved in 184 mL hot DMSO. The solution is diluted with 368 mL boiling water while a beige solid precipitates. The mixture is allowed to reach room temperature while stirring. The suspension is cooled to 5° C. and the solid filtered. The solid is washed with 300 mL water, and dried at 5 mbar and 40° C. for 24 hours and further dried at 40° C. for 20 hours at 0.1 mbar. The so obtained material is cadazolid in form A.

TABLE 1

Characterization data for compound in crystalline form A from Example 1.1

| Technique | Data Summary | Remarks |
| --- | --- | --- |
| XRPD | Crystalline, form A | see FIG. 1 |
| $^1$H-NMR | Consistent | — |
| DSC with 10° C./min | DSC measurement is run on a sample of form A after drying under dry nitrogen gas for 3 days. The sample exhibits a melting peak at 239° C. with a melting enthalpy of ΔH = 91 J/g. | — |
| GVS1 at 25° C. | A continuous weight change of the sample between 0% and 95% r.h. is observed. It amounts to a maximum difference in water content of approximately 0.5 mol/mol. No hysteresis is observed. The water content of the solid increases from 0.81 to 1.81% when going from 40% r.h. to 95% r.h. and the sample is considered as being slightly hygroscopic (adapted methodology to account for dynamic type measurement, classification according to Pharm. Eur 8.0, section 5.11., hygroscopicity) | — |

Example 1.2: Preparation of Crystalline Form A of Cadazolid 116 mg of solid cadazolid are dissolved in 5 mL water and 5 mL DMSO at about 150° C. The solution is allowed to cool back to r.t., which leads to the precipitation of a solid after only a few minutes. The solid is filtered off after 3 days and dried at r.t./8 mbar for 45 min. The obtained material is cadazolid in form A.

Example 1.3: Preparation of Crystalline Form A of Cadazolid

Upon drying under vacuum at r.t., crystalline form B of cadazolid (obtainable as described in Examples 2.1 and 2.2) transforms into crystalline form A thereof.

Example 2.1: Preparation of Crystalline Form B of Cadazolid

A suspension of 198 mg of cadazolid in form A is stirred at r.t. in 2 mL of water for 3 days. The solid is filtered off and analyzed without drying. The obtained material is cadazolid in form B.

TABLE 2

Characterization data for compound in crystalline form B from Example 2.1

| Technique | Data Summary | Remarks |
| --- | --- | --- |
| XRPD | Crystalline, form B | see FIG. 2 |
| $^1$H-NMR | Consistent | — |
| GVS2 at 25° C. | In GVS, a continuous weight loss of approx. 30% during 6 h equilibration at 95% r.h. is observed; an additional, accelerated weight loss of approx. 15% is observed upon lowering the r.h. at a rate of 5%/h. At 80% r.h., the water content of form A is reached. | — |

Example 2.2: Preparation of Crystalline Form B of Cadazolid 27 mg of cadazolid in form A and 25 mg of cadazolid in form C (obtainable as described in Example 3) are suspended in 1 mL $H_2O$, treated for 5 min in an ultrasound bath and agitated at 25° C. The solid is filtered off after 5 days and analyzed. The obtained material is cadazolid in form B.

Example 3: Preparation of Crystalline Form C of Cadazolid

A solution of approx. 80 mg of cadazolid in form A in 0.5 mL DMSO is added to 10 mL 2-PrOH while stirring. A precipitate forms instantaneously. The solid is filtered off after 2 min, washed with 2-PrOH and dried for 30 min at r.t. and 3 mbar. 50 mg of product is obtained which is cadazolid in form C.

TABLE 3

Characterization data for compound in crystalline form C from Example 3

| Technique | Data Summary | Remarks |
|---|---|---|
| XRPD | Crystalline, form C | see FIG. 3 |
| $^1$H-NMR | Consistent | — |
| DSC | Measurement at 10° C./min: A small endotherm is observed at 199° C. ($\Delta$H = 4 J/g), followed by a very small exotherm and a melting at 239° C. ($\Delta$H = 90 J/g). The latter corresponds to melting of form A. Measurement at 100° C./min: A melting point of 221° C. is attributed to form C melting. | — |
| GVS1 at 25° C. | The water content of the solid increases from 0.33 to 2.52% when going from 40% r.h. to 95% r.h. and the sample is considered as being hygroscopic (adapted methodology to account for dynamic type measurement, classification according to Pharm. Eur 8.0, section 5.11., hygroscopicity). | — |

Example 4: Preparation of Amorphous Cadazolid 103 mg of cadazolid in form A are sealed in a glass vial under gaseous nitrogen and heated to 240° C. for 5 min. Upon cooling back to r.t., a transparent, brownish solid is obtained which is cadazolid in amorphous form.

TABLE 4

Characterization data for compound in amorphous state from Example 4

Figure 4:
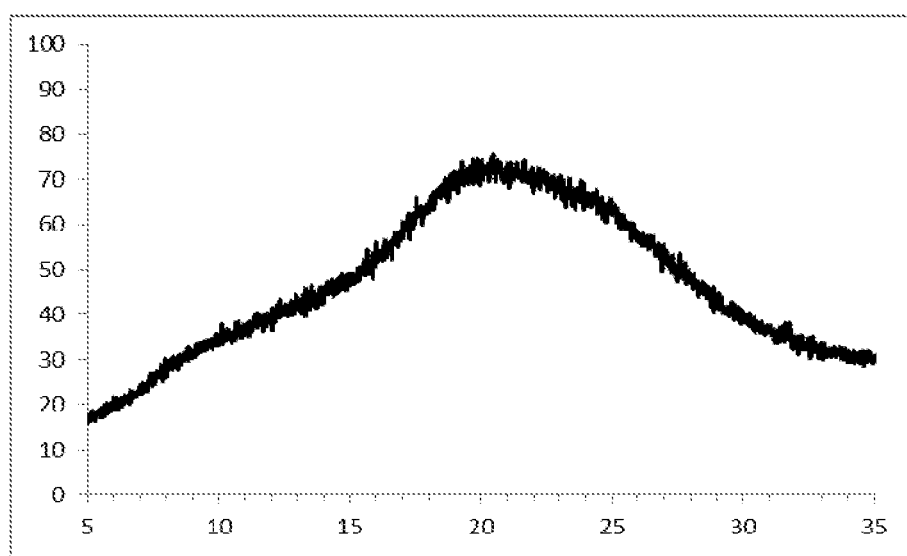
FIG. 4 shows the X-ray powder diffraction diagram of cadazolid in amorphous form, wherein the X-ray powder diffraction diagram is displayed against Cu Kα radiation. In the diagram the angle of refraction 2θ is plotted on the horizontal axis and the intensity (cps) on the vertical axis. The diffraction diagram shows a broad halo type signal, typical for amorphous materials.

| Technique | Data Summary | Remarks |
|---|---|---|
| XRPD | Amorphous, absence of any sharp reflections | see FIG. 4 |
| $^1$H-NMR | Consistent | — |
| DSC at 10° C./min | The sample exhibits a glass transition at 102° C. ($\Delta$Cp = 0.38 J/(g K)), followed by recrystallization at 162° C. ($\Delta$H = −60 J/g) and a melting point at 238° C. ($\Delta$H = 90 J/g). The latter corresponds to melting of form A. | — |
| GVS1 at 25° C. | A weight increase of about 7% (circa 2.3 equivalents H$_2$O) between 0% and 95% r.h. with a significant hysteresis observed in GVS. The sample remains amorphous as tested by a post GVS XRPD. The water content of the solid increases from 1.8 to 7.17% when going from 40% r.h. to 95% r.h. and the sample is considered as being hygroscopic (adapted methodology to account for dynamic type measurement, classification according to Pharm. Eur 8.0, section 5.11., hygroscopicity). | — |

Example 5: Pharmaceutical Formulation of Cadazolid Form A

Crystalline form A of cadazolid, calcium hydrogen phosphate dihydrate, sucrose, sodium carboxymethylcellulose, colloidal silicon dioxide and flavor are first blended and then granulated by roller compaction. Colorant, sucrose and colloidal silicon dioxide are subsequently added to the granules prior to final blending. The final mixture is blended prior to transfer to a sachet filling machine. The final sachet has a composition as shown in Table 5. The sachet content is suspended in water directly before oral administration.

TABLE 5

| Ingredient | % w/w | Function |
|---|---|---|
| Crystalline form A of cadazolid | 1.5-50 | Active ingredient |
| Calcium hydrogen phosphate dihydrate | 0.25-30 | Filler/Turbidity agent |
| Sucrose | 48-86 | Diluent/Sweetener |
| Sodium carboxymethylcellulose | 0.1-1 | Thickener |
| Colloidal silicon dioxide | 0.1-10 | Glidant/Suspending agent |
| Flavor | 0.2-0.4 | Flavoring |
| Colorant | 0.06-0.1 | Coloring |

Example 6.1: Relative Thermodynamic Stability of Crystalline Forms of Cadazolid The relative thermodynamic stability of polymorphic forms can be deduced from their melting points and melting enthalpies (L. Yu, *Journal of Pharmaceutical Sciences* 84 (1995) 966-974). These values are summarized in the Table 6 below for form A and C of cadazolid:

TABLE 6

| Form | m.p. | $\Delta$H [J/g] | $\Delta$S [J/(g K)] |
|---|---|---|---|
| A | 239° C. | 91 | 0.1777 |
| C | 221° C. | 94 | 0.1903 |

The form with the higher melting point disposes of the lower melting enthalpy. This is a clear indication for an enantiotropic system of polymorphic forms with form A being the more thermodynamically stable form at room temperature.

Example 6.2: Suspension Equilibration Experiments

The following suspension equilibration experiments are performed in organic solvent (mixture of methanol and dichloromethane) and in water:

Example 6.2.1

26 mg of cadazolid in form A and 25 mg of cadazolid in form C are suspended in 1 mL MeOH/CH$_2$Cl$_2$ 1:3 and agitated at 25° C. The solid is filtered off after 5 days and is cadazolid in form A.

Example 6.2.2

27 mg of cadazolid in form A and 26 mg of cadazolid in form C are suspended in 1 mL MeOH/CH$_2$Cl$_2$ 1:3 and agitated at 5° C. for 2 days. Some solid is isolated by drying on a filter paper and consists of cadazolid in form A.

Example 6.2.3

29 mg of cadazolid in form A and 26 mg of cadazolid in form C are suspended in 1 mL H$_2$O, treated for 5 min in an ultrasound bath and agitated at 5° C. for 2 days. Some solid is isolated by drying on filter paper and consists of cadazolid in form B.

Form A results from experiments in non-aqueous organic solvent at 25° C. and at 5° C., while form B is formed at said temperatures in water (cf. Examples 6.2.1, 6.2.2, 6.2.3 and 2.2). Based on the results of said experiments and on the information on stability of form B (GVS2 data in Table 2), it can be concluded that at 25° C. form A is thermodynamically more stable than form C both at low and high relative humidity.

The invention claimed is:

1. A crystalline form of cadazolid, characterized by one of the following X-ray powder diffraction patterns: (a) an X-ray powder diffraction pattern having peaks at the following angles of refraction 2θ: 7.9°, 14.7° and 27.2°; (b) an X-ray powder diffraction pattern having peaks at the following angles of refraction 2θ: 7.9°, 14.4° and 27.9°; or (c) an X-ray powder diffraction pattern having peaks at the following angles of refraction 2θ: 7.7°, 15.5° and 24.4°; wherein the X-ray powder diffraction patterns are measured using a Cu Kα (1.5418 Å) source; or mixtures of such crystalline forms.

2. A crystalline form according to claim 1, characterized by an X-ray powder diffraction pattern having peaks at the following angles of refraction 2θ: 7.9°, 14.7° and 27.2°, wherein the X-ray powder diffraction pattern is measured using a Cu Kα (1.5418 Å) source.

3. The crystalline form according to claim 2, characterized by an X-ray powder diffraction pattern having peaks at the following angles of refraction 2θ: 7.9°, 9.1°, 14.7°, 19.7° and 27.2°, wherein the X-ray powder diffraction pattern is measured using a Cu Kα (1.5418 Å) source.

4. The crystalline form according to claim 2, characterized by an X-ray powder diffraction pattern having peaks at the following angles of refraction 2θ: 7.9°, 9.1°, 14.7°, 15.9°, 17.9°, 19.7°, 24.5°, 24.9°, 25.5° and 27.2°, wherein the X-ray powder diffraction pattern is measured using a Cu Kα (1.5418 Å) source.

5. The crystalline form according to claim 2, characterized in that it essentially shows an X-ray powder diffraction pattern as depicted in FIG. 1.

6. The crystalline form according to claim 2, characterized by a melting point of about 239° C. as determined by differential scanning calorimetry.

7. A crystalline form according to claim 1, characterized by an X-ray powder diffraction pattern having peaks at the following angles of refraction 2θ: 7.9°, 14.4° and 27.9°, wherein the X-ray powder diffraction pattern is measured using a Cu Kα (1.5418 Å) source.

8. The crystalline form according to claim 7, characterized by an X-ray powder diffraction pattern having peaks at the following angles of refraction 2θ: 7.9°, 14.4°, 15.9°, 20.2°, and 27.9°, wherein the X-ray powder diffraction pattern is measured using a Cu Kα (1.5418 Å) source.

9. The crystalline form according to claim 7, characterized by an X-ray powder diffraction pattern having peaks at the following angles of refraction 2θ: 7.9°, 9.1°, 14.4°, 15.9°, 17.9°, 18.5°, 20.2°, 22.5°, 26.4° and 27.9°, wherein the X-ray powder diffraction pattern is measured using a Cu Kα (1.5418 Å) source.

10. The crystalline form according to claim 7, characterized in that it essentially shows an X-ray powder diffraction pattern as depicted in FIG. 2.

11. A crystalline form according to claim 1, characterized by an X-ray powder diffraction pattern having peaks at the following angles of refraction 2θ: 7.7°, 15.5° and 24.4°, wherein the X-ray powder diffraction pattern is measured using a Cu Kα (1.5418 Å) source.

12. The crystalline form according to claim 11, characterized by an X-ray powder diffraction pattern having peaks at the following angles of refraction 2θ: 7.7°, 14.6°, 15.5°, 16.3° and 24.4°, wherein the X-ray powder diffraction pattern is measured using a Cu Kα (1.5418 Å) source.

13. The crystalline form according to claim 11, characterized by an X-ray powder diffraction pattern having peaks at the following angles of refraction 2θ: 7.7°, 10.9°, 14.6°, 15.5°, 16.3°, 18.1°, 21.1°, 24.4°, 25.1° and 27.4°, wherein the X-ray powder diffraction pattern is measured using a Cu Kα (1.5418 Å) source.

14. The crystalline form according to claim 11, characterized in that it essentially shows an X-ray powder diffraction pattern as depicted in FIG. 3.

15. The crystalline form according to claim 11, characterized by a melting point of about 221° C. as determined by differential scanning calorimetry.

16. A composition comprising a crystalline form according to claim 1, further comprising at least one pharmaceutically acceptable excipient.

* * * * *